(12) United States Patent
Loh et al.

(10) Patent No.: US 9,713,333 B2
(45) Date of Patent: Jul. 25, 2017

(54) **PRODUCT AND METHOD FOR MANAGING *GANODERMA* DISEASE IN OIL PALM**

(71) Applicant: Agribolics Technology Sdn. Bhd., Serdang, Selangor Darul Ehsan (MY)

(72) Inventors: Siew Fan Loh, Selangor (MY); Mohd Amid Fursan bin Abdullah, Selangor (MY)

(73) Assignee: Agribolics Technology Sdn. Bhd. (MY)

( * ) Notice: Subject to any disclaimer, the term of this patent is extended or adjusted under 35 U.S.C. 154(b) by 0 days.

(21) Appl. No.: 14/399,881

(22) PCT Filed: May 8, 2013

(86) PCT No.: PCT/MY2013/000092
§ 371 (c)(1),
(2) Date: Nov. 7, 2014

(87) PCT Pub. No.: WO2013/169092
PCT Pub. Date: Nov. 14, 2013

(65) Prior Publication Data
US 2015/0111748 A1    Apr. 23, 2015

(30) Foreign Application Priority Data

May 8, 2012 (MY) .......................... PI2012002018

(51) Int. Cl.
*A01N 25/00* (2006.01)
*A01N 63/00* (2006.01)
*A01N 63/02* (2006.01)
*C12N 1/20* (2006.01)

(52) U.S. Cl.
CPC ............. *A01N 63/02* (2013.01); *C12N 1/20* (2013.01)

(58) Field of Classification Search
None
See application file for complete search history.

(56) References Cited

U.S. PATENT DOCUMENTS 5,602,036 A * 2/1997 Criddle .................... C12N 1/20
435/252.1

FOREIGN PATENT DOCUMENTS

| JP | 2004346028 A | 12/2004 |
| JP | 2005289943 A | 10/2005 |
| JP | 2005289944 A | 10/2005 |
| JP | 2005289945 A | 10/2005 |
| WO | WO2011002270 A1 | 1/2011 |

OTHER PUBLICATIONS

A. Susanto, et al., Mycopathologia, 2005, vol. 159, pp. 153-157.

* cited by examiner

*Primary Examiner* — Alton Pryor
(74) *Attorney, Agent, or Firm* — Head, Johnson, Kachigian & Wilkinson, PC

(57) ABSTRACT

A product for treating and/or preventing diseases such as basal stem rot caused by *Ganoderma* infection, in plants such as oil palms, comprising a growth medium used to grow *Pseudomonas fluorescens* bacteria, said growth medium including palm oil mill effluent.

9 Claims, 3 Drawing Sheets

PRODUCT AND METHOD FOR MANAGING *GANODERMA* DISEASE IN OIL PALM

FIELD OF INVENTION

The invention relates to a product and method for managing *Ganoderma* disease in oil palm.

Although the following description relates almost exclusively to managing *Ganoderma* disease in oil palm, it will be appreciated by those skilled in the art that the invention could be used to treat other diseases of other plants.

BACKGROUND

Basal stem rot (BSR) is a disease of oil palms caused by species of the fungus *Ganoderma*, and in particular *G. boninense*. BSR is considered to be the most destructive disease in the oil palm industry in Southeast Asia.

Infections appear to advance more quickly in subsequent generations of oil palm planting because of accumulation of inoculums, and the possibility of evolution of more virulent strains of the pathogen. The mating system of *G. boninense* strongly favours outcrossing and this provides a possible mechanism for the selection of pathogen virulence.

Traditionally, the disease was managed by attempting to minimise the incidence and mitigating the impact of the disease. More recently, biological controls such as antagonistic fungi e.g. *Trichoderma* species have been tested, but although they appeared promising at first, there were issues with sustainability and persistency in the field.

An aim of the invention is therefore to provide a product and method for managing the oil palm disease which overcomes the above issues.

SUMMARY OF INVENTION

In an aspect of the invention, there is provided an application product for treating and/or preventing diseases of plants characterised in that the product comprises a growth medium used to grow *Pseudomonas fluorescens* bacteria.

Advantageously the *Pseudomonas fluorescens* bacteria produce secondary metabolites with anti-microbial activity and induce systemic resistance of treated plants, which thereby help in treating and/or preventing diseases of plants when applied thereto.

In one embodiment the application product comprises *Pseudomonas fluorescens* bacteria from the growth medium.

In one embodiment the bacteria in the product are substantially dead. In an alternative embodiment the bacteria in the product are live.

In a further embodiment the growth medium is filtered to remove the bacteria. As the secondary metabolites are present in the medium, the bacteria may be considered to be superfluous to the disease control.

In one embodiment the application product includes any or any combination of sorbitol, sodium hydrogen phosphate, a surfactant, palm oil, glycerol residue, potassium sorbate, and/or the like. These components help preserve the activity of the secondary metabolites, and also to help the penetration of the metabolites through the leaf surface after spraying.

In a further embodiment the application product comprises sago pearls. Typically the pearls comprise growth medium and live bacteria.

In one embodiment the pH of the application product is around pH5 to about pH7.

In one embodiment the plants are oil palm species. Typically the species is *Elaeis guineenis*.

In one embodiment the disease is caused by fungi such as *Ganoderma* species. Typically the disease is basal stem rot.

In one embodiment the growth medium includes palm oil mill effluent and any or any combination of glycerol residue, crude glycerol, glycerol, glycerine, soy flour, jaggery (brown sugar), soybean oil, ammonium sulphate, potassium hydrogen phosphate, sodium hydrogen phosphate, magnesium sulphate, and/or zinc sulphate.

Advantageously the growth medium is much more effective for aerobic growth of the *Pseudomonas fluorescens* bacteria and production of secondary metabolites with anti-fungal activity therefrom, compared to a traditional artificial medium.

Palm oil mill effluent is obtained during palm oil milling process. It is estimated that for each ton of crude palm oil that is produced, 5-7.5 tonnes of water are required, and more than 50% of this water ends up as palm oil mill effluent. The effluent is a colloidal suspension containing 95-96% water, 0.6-0.7% oil and 4-5% total solids. Thus a further advantage of the invention is that it makes use of the waste palm oil mill effluent.

The bacterium ATCC BAA-477 is both known and readily available. The bacterium has been deposited as *Pseudomonas fluorescens migula* (Pf-5) pursuant to the Budapest Treaty on the International Recognition of the Deposit of Microorganisms for Purposes of Patent Procedure. Details of the bacterium can be found at https://www.atcc.org/Products/A11/BAA-477.aspx#history and by contacting American Type Culture Collection (ATCC), 10801 University Boulevard, Manassas, Va. 20110.

In a further aspect of the invention, there is provided a method of treating and/or preventing diseases of plants by use of an application product comprising a growth medium used to grow *Pseudomonas fluorescens*.

In one embodiment the application product is applied to any or any combination of soil, fertiliser, pre-germination seeds, seedlings, saplings and/or trees.

In one embodiment seeds are soaked in the application product. Typically the seeds or seedlings are submerged in the application product for about an hour.

In one embodiment the application product is sprayed onto the leaves of the plants. Typically the application product is sprayed onto the leaves on a regular basis, such as weekly.

In one embodiment the application product is injected into the trunks of trees. Typically the application product is diluted and sprayed on diseased areas of the trunks of trees. This may be used to treat infected trees.

In one embodiment the growth medium comprises palm oil mill effluent, in which *Pseudomonas fluorescens* bacteria are grown, typically at around 30° C. for about 2 days, although it will be appreciated that other suitable temperatures and times could be used.

In one embodiment feed medium is added to the growth medium during growth of the bacteria.

In one embodiment the feed medium comprises any or any combination of glycerine and jaggery. Typically the feed volume starts around 6 hours after inoculation of the *Pseudomonas fluorescens* bacteria into the growth medium, and continues for around 12 hours.

In one embodiment the application product comprises around 0.5% (v/v) of the growth medium. Typically the growth medium is diluted in water.

If a different media to the palm oil mill effluent is used, it has been found that a more concentrated solution of bacteria (around 10-15%) is required for the same activity. Thus the use of palm oil mill effluent improves the efficiency by around 20-30 fold.

Ideal growth of *Pseudomonas fluorescens* bacteria occurs at around 28-30° C., whereas death tends to occur at temperatures of 40-45° C. or higher.

In one embodiment the *Pseudomonas fluorescens* bacteria are heat-treated to substantially kill the same, prior to forming the application product, typically at around 70° C. for about 30 minutes, although it will be appreciated that other suitable temperatures and times could be used.

In a yet further aspect of the invention, there is provided a method of manufacturing a product for treating and/or preventing diseases of oil palms comprising the steps of:
  growing *Pseudomonas fluorescens* bacteria in a growth medium;
  mixing and/or diluting the growth medium with other components to form an application product which can be applied to soil, fertiliser, seeds, seedlings, saplings and/or trees;
  characterised in that the growth medium comprises palm oil mill effluent.

In a further aspect of the invention there is provided a method of treating basal stem rot via application of *Pseudomonas fluorescens*.

BRIEF DESCRIPTION OF DRAWINGS

It will be convenient to further describe the present invention with respect to the accompanying drawings that illustrate possible arrangements of the invention. Other arrangements of the invention are possible, and consequently the particularity of the accompanying drawings is not to be understood as superseding the generality of the preceding description of the invention.

DETAILED DESCRIPTION

Figure 1:
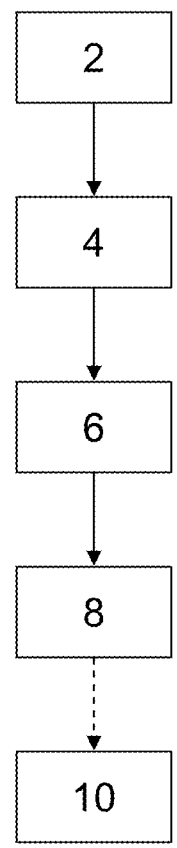
FIG. 1 is a schematic view of a method of manufacturing a product for treating and/or preventing diseases of oil palms according to an embodiment of the invention.

With reference to FIG. 1 there is provided an overview of a method of manufacturing a product for treating and/or preventing diseases of oil palms, whereby palm oil mill effluent is filtered (200-mesh) to remove large particles, and a growth medium based on the same is then inoculated with *Pseudomonas fluorescens* bacteria and incubated (2) for 2 days at 30° C.

This solution is then heat-treated (4) at around 70° C. for about 30 minutes to substantially kill the bacteria, then diluted (6) in water, containing a wetting agent, to a final volume of around 0.5% (v/v) to around 2.0% (v/v).

The diluted mixture can then be mixed (8) with various components to form an application product, which can then be applied (10) to oil palms to treat and/or preventing diseases such as basal stem rot, by inhibiting growth of fungi such as *Ganoderma boninense*.

Stock Culture and Seed Preparation:

*Pseudomonas fluorescens* ATCC BAA-477 (Pf-5) was cultivated on tryptic soy agar (TSA) (containing 10 µg/mL chloramphenicol) as stock culture. A few Pf-5 colonies from the TSA plate were inoculated onto palm oil mill effluent-glycerol residue (POME-GR) based agar to test its viability.

Pf-5 seed was prepared by inoculating a few colonies from POME-GR based agar to POME-GR based medium and incubated for 16 h in a shaker-incubator at around 28° C. and about 280 rpm. The Pf-5 seed culture was used at a concentration of 0.5% (v/v) to inoculate the subsequent fermentation step.

Culture Fermentation

The growth medium for fermentation was prepared in a 200 L bioreactor, comprising the following components:
  87.5% (v/v) palm oil mill effluent (POME)
  0.5% (v/v) glycerine
  0.83% (w/v) glycerol residue
  0.2% (w/v) jaggery
  0.1% (v/v) palm oil
  0.02% (w/v) $ZnSO_4$
  0.05% (w/v) $K_2HPO_4$
  0.3% (w/v) $NH_4SO_4$ The pH of the medium was adjusted to 7.2 by the addition of KOH and then sterilized by autoclave at 121° C. for 15 minutes.

Seed culture was inoculated to the medium when it had cooled to room temperature and then incubated at 28° C. for 48 hours.

A feed medium was prepared comprising the following components diluted in water:
  15% (v/v) glycerin
  3% (w/y) jaggery The feed medium was fed at a rate of 27.8 mL/min, starting at 6 hours after inoculation (0.5% volume of the main medium volume) and fed continuously for another 12 hrs (total feed volume was 10% of the main medium volume). The pH was set at 7.2 by using KOH. Air flow was set at 15 L/min, and stir rate was set at 200 rpm.

Composition of Application Product

An application product known as 'Bio-Striker' comprises the growth medium and the following components;
  3% (w/v) Sorbitol,
  1% (w/v) $NaH_2PO_4$,
  0.2% (v/v) Silwet HS-429 (Momentive Inc., USA),
  1.0% (v/v) SLK-408 (Jiande Silicone Import & Export Co., Ltd, China),
  0.5% (v/v) palm oil,
  0.1% (w/v) glycerol residue,
  0.5% (w/v) potassium sorbate.

The pH is adjusted to a value of around 5. The bacteria in the growth medium are killed via heat-treatment prior to addition of the other components. SLK and Silwet are surfactants meant to help wetting on plant surface and help penetration of the product.

The additives help preserve the metabolites and increase penetration of the metabolites through the leaf surface after spraying. The use of Silwet HS-429 or an equivalent surfactant is to help increase plant surface penetration.

An alternative formulation ('Bio-Striker live') comprises the growth medium and the following components;
  9% (w/v) Sorbitol,
  3% (w/v) $NaH_2PO_4$,
  0.2% (v/v) Silwet HS-429 (Momentive Inc., USA),
  1.0% (v/v) SLK-408 (Jiande Silicone Import & Export Co., Ltd, China),
  0.5% (v/v) palm oil, The pH is adjusted to a value of around 5.5. The bacteria are live in this formulation wherein the high sorbitol and NaH$_2$PO$_4$ concentration and acidic pH help to halt bacterial growth and preserve the enzymes.

A further application product ('Gano-Striker') comprises the growth medium containing live bacteria, without any additional adjuvants.

An application product known as 'Ferti-Booster' (or 'Gano-Soil') can also be formulated. After the fermentation process in POME-based medium, the culture is not heat-killed. About 800 ml of the culture is poured into 1 kg of sago pearls (about 3 mm in diameter).

The sago pearls were mixed and left alone for about 3 min to allow the culture broth to be absorbed into the pearls. Then the sago pearls were spread thinly and air dried under a blowing fan at ambient temperature overnight.

The next day the pearls were turned over with a spatula and drying continues for a few more hours to allow uniform drying. The drying is done when about 65-70% of water has been evaporated.

The Ferti-Booster product can be mixed into organic fertilizer such as poultry manure. The Gano-Soil product can be applied by spreading it on soil near an oil palm tree.

Figure 2A:
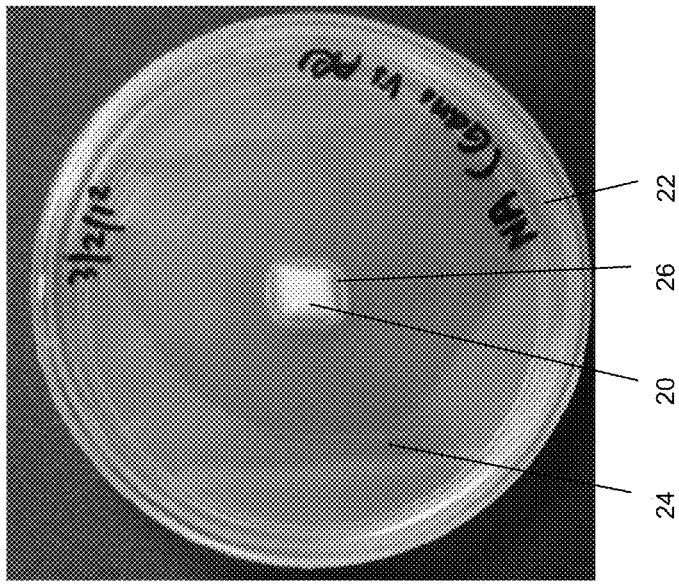
FIG. 2 is an overhead view of a petri dish illustrating (a) the natural growth of *Ganoderma boninense* and (b) the inhibitory effect of *Pseudomonas fluorescens* metabolites on the growth of *Ganoderma boninense*.
Figure 2B:
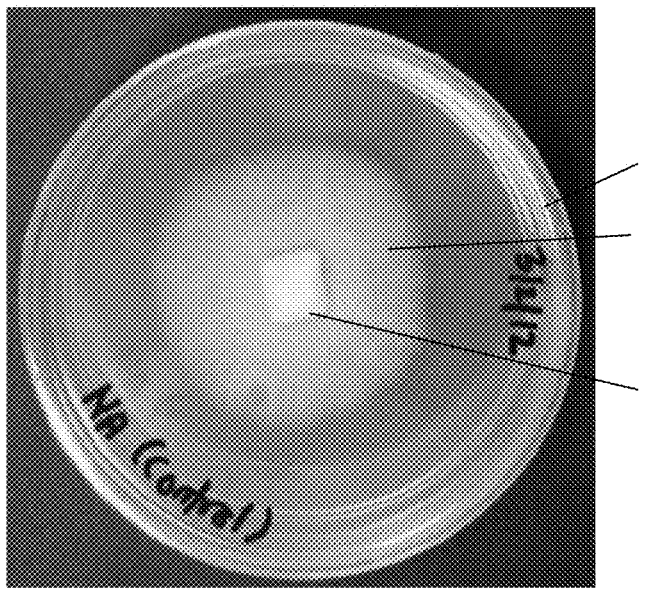

With reference to FIGS. 2a-b, a plug 20 containing micelia of Ganoderma boninense was placed in the middle of a petri dish 22 containing nutrient agar. On one of the petri dishes (FIG. 2b), Pf5 bacteria was streaked 24 at 2.5 cm distance from the plug. On the other plate (FIG. 2a) only Ganoderma was cultured, as a control.

After 7 days incubation at 28° C., the radius of Ganoderma micelial growth 26 was measured for both plates. The inhibition of Ganoderma growth by Pf5 was projected as percentage inhibition of radial growth (PIRG):

$$PIRG=(RC-RI)/RC\times 100;$$

where RC=micelial radius in control plate,
and RI=micelial radius in treatment plate.

The results show that PIRG for Pf5 vs Ganoderma boninense was 90.2%.

With reference to FIG. 3 oil palm seedlings 30 are shown, grown from seeds divided into four treatment groups in order to test the effect of Pf5 formulations in controlling Ganoderma boninense infection; each group containing ten germinated seeds.

Figure 3A:
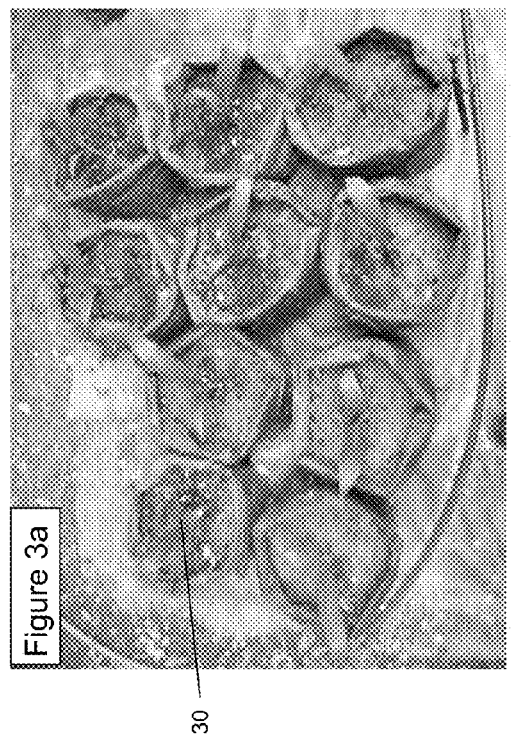
FIG. 3 is an overhead view of ten oil palm seedlings: (a) without treatment (b) treated with an application product according to the invention; (c) treated with *Ganoderma boninense* and an application product according to the invention; and (d) treated with *Ganoderma boninense*.
Figure 3B:
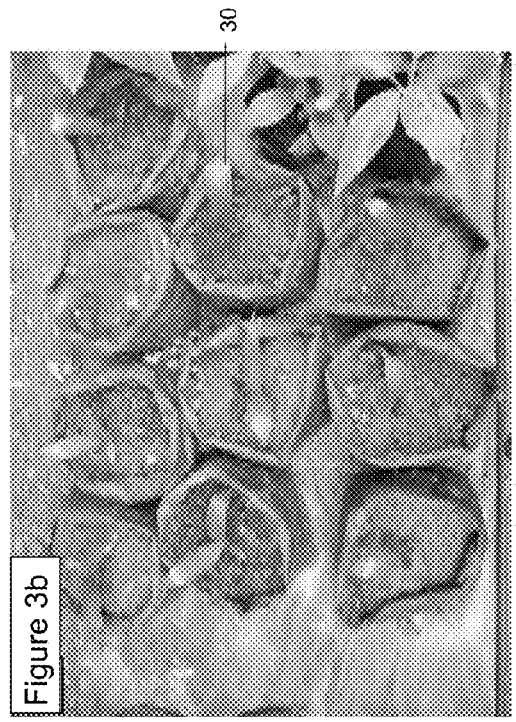
Figure 3C:
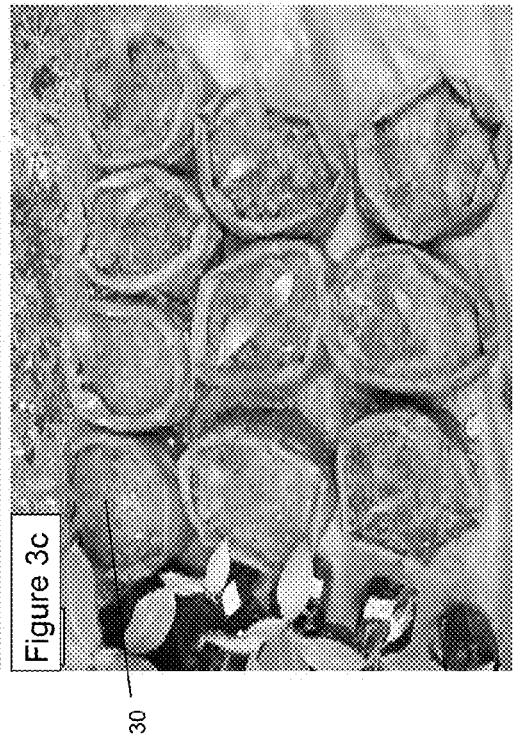
Figure 3D:
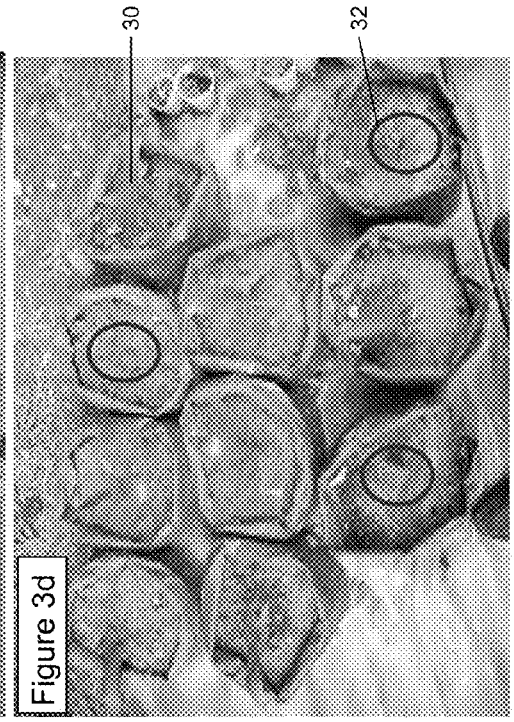

The four treatment groups are Untreated (FIG. 3a), Pf5 treatment alone (FIG. 3b), Pf5 treatment and Ganoderma (FIG. 3c); and Ganoderma alone (FIG. 3d).

The germinated seeds (GH 500 FS2; D×P) were obtained from Sime Darby Seeds & Agricultural Services Sdn Bhd and used on the same day. The Ganoderma treated seeds were infected according to MPOB bulletin (MPOB TT No. 314). The artificial infection source of Ganoderma was rubber wood blocks (6×6×6 cm) covered with Ganoderma boninense obtained from MPOB (Malaysian Palm Oil Board).

For the Pf5 treatments, germinated seeds were submerged in 3% Bio-Striker (containing killed Pf5 formulation) for 1 hour. The soil surface was applied with 4 teaspoons of Ferti-Booster (containing live Pf5 in granulated form) prior to planting. Thereafter, Bio-Striker (2% concentration) was sprayed (about 1 ml/plant) weekly, beginning from when the shoots emerged from the soil. One teaspoon (about 0.5 g/plant) Ferti-Booster was applied on the soil surface every 2 weeks.

After three months FIG. 3d shows that three oil palm seedlings or 30% of seedlings appear to be stunted (circled 32), and have desiccating or browning leaves; typical symptoms of oil palm seedlings that are infected with Ganoderma boninense. Based on MPOB bulletin No. 314 more of the infected seedlings in FIG. 3d would be expected to show the foliar disease symptoms over time e.g. 45-60% at 6 months.

However, oil palm seedlings in FIG. 3c did not show the disease symptoms, confirming that the Pf5 treatments are inhibiting Ganoderma infection.

Application to Trees

For older oil palms, Gano-Striker can be injected into the trunk of the tree, and diluted to 1% (v/v) in water for spraying onto areas of the trunk that are showing Ganoderma disease symptoms i.e. conks or basidiocarp.

In a field trial, 50 trees were selected showing symptoms of sickness such as older fronds withering, drooping and turning brown; as older fronds continue to die, younger leaves may wilt and the tips may turn brown. The selected trees were marked (GPS locations of each tree where possible) and the severity of disease and fresh fruit bunch (FFB) yield of each selected tree was noted.

Gano-Striker was resuspended by inverting twice to wet the whole vial/bottle. The suspension appeared as a dark brown solution. Each opened vial/bottle was used up within a day and not stored for later use.

Using a proper size drill bit (5/16"), a hole was drilled at a slight downward angle (about 20-30°) into the trunk to the proper depth of about 9 inches.

Using a syringe (without needle attached) filled with Gano-Striker solution, 12 ml of the Gano-Striker solution was administered. The hole was plugged with a rubber stopper.

Each of the selected trees was treated with 6-12 injections of Gano-Striker for the first application e.g. two injection sites at 3-4 feet above ground (injection sites on opposing sides of the trunk) and 4-10 injection sites at 1-2 feet above ground (each injection site is made at 1-1.5 feet interval around the circumference of the trunk; as near to the mushroom bodies as possible).

To treat the visible Ganoderma conks, Gano-Striker was diluted with non-chlorinated water to 1% (v/v) concentration and sprayed on the conks. This helped to reduce spread of the fungus through aerial dispersement. Treatments were repeated every time injections are performed.

A month later, the same injection sites were redrilled to increase the depth by ¾-1 inch and new 12 ml of Gano-Striker solution was injected. Three months later, treatments were continued with double injections (at 3-4 feet above ground) every 2 months 2 times.

Treatments were repeated again after a 12-month break if the disease symptoms worsened. Depending on the severity of BSR, recovery of the diseased trees could be observed 6 to 18 months after beginning of treatment or longer.

After the trees recovered as indicated by increased FFB yield, annual treatments are needed to provide continuous protection from recurring BSR. Once a year, two simultaneous injections of Gano-Striker can be made at a height of 3-4 feet above ground.

Application to Trees

Gano-Soil was applied at the same time as applying fertilizer. If biofertilizer was applied, Gano-Soil was applied to the soil first before being covered by the biofertilizer. If chemical fertilizer was applied, Gano-Soil was applied at a distance of 0.3 meter (1 foot) away from the fertilizer and covered with 3-5 cm of soil. About 12 grams of Gano-Soil was applied per tree.

The same amount of Gano-Soil was applied every 3 months.

Note that trees that have very severe BSR may not respond to treatment, thus may continue to deteriorate and die. In addition some trees with severe BSR may topple over by high wind due to rotted trunk. Thus, mounding of the treated trees with soil may be recommended to increase tree stability.

Two treatment regiments are suggested—Inj A and Inj B that represent low rate and high rate application treatments. The Inj A Series (6 injections initially) is suggested for low-medium BSR severity, while Inj B (12 injections initially) for medium-high BSR severity.

It will be appreciated by persons skilled in the art that the present invention may also include further additional modifications made to the device which does not affect the overall functioning of the device.

The invention claimed is:

1. An application product used to treat and/or prevent diseases of plants, the product comprises:

a growth medium comprising palm oil mill effluent, said palm oil mill effluent being waste effluent generated during palm oil milling process;

said growth medium having been used to grow *Pseudomonas fluorescens* bacteria strain ATCC BAA-477; and wherein the product includes live *Pseudomonas fluorescens* bacteria strain ATCC BAA-477 from the growth medium.

2. An application product according to claim 1 wherein the *Pseudomonas fluorescens* bacteria strain ATCC BAA-477 comprise dead bacteria.

3. An application product according to claim 1 wherein the product comprises any of sorbitol, sodium hydrogen phosphate, a surfactant, palm oil, glycerol residue, potassium sorbate, and/or sago pearls.

4. A method of treating and/or preventing diseases of plants comprising applying the application product as set forth in claim 1 to soil, fertiliser, pre-germination seeds, seedlings, saplings and/or trees.

5. A method according to claim 4 wherein the seeds or seedlings are soaked in the application product for about an hour and/or the application product is sprayed onto leaves of the plants and/or the application product is injected into trunks of the trees or combinations thereof.

6. A method according to claim 4 wherein a feed medium comprising glycerine and/or jaggery is added to the growth medium.

7. A method according to claim 4 wherein the *Pseudomonas fluorescens* bacteria are heat-treated to substantially kill the *Pseudomonas fluorescens* bacteria, prior to forming the application product.

8. A method of treating basal stem rot via application of *Pseudomonas fluorescens* ATCC BAA-477 comprising applying the application product as set forth in claim 1 to soil, fertilizer, pre-germination seeds, seedlings, saplings and/or trees.

9. A method of manufacturing a product for treating and/or preventing diseases of oil palms comprising the steps of:

growing bacteria in a growth medium comprising palm oil mill effluent;

mixing and/or diluting the growth medium with other components to form an application product which can be applied to soil, fertiliser, seeds, seedlings, saplings and/or trees;

wherein the bacteria are *Pseudomonas fluorescens* bacteria strain ATCC BAA-477.

* * * * *